US012758529B2

(12) United States Patent
Zhou et al.

(10) Patent No.: US 12,758,529 B2
(45) Date of Patent: Oct. 13, 2026

(54) USE OF EDARAVONE IN TREATMENT OF AUTISM SPECTRUM DISORDER

(71) Applicant: Shanghai Auzone Biological Technology Co., Ltd., Shanghai (CN)

(72) Inventors: Yi Zhou, Suzhou City (CN); Xin Ye, Suzhou City (CN)

(73) Assignee: Shanghai Auzone Biological Technology Co., Ltd., Shanghai (CN)

( * ) Notice: Subject to any disclaimer, the term of this patent is extended or adjusted under 35 U.S.C. 154(b) by 304 days.

(21) Appl. No.: 18/702,278

(22) PCT Filed: Oct. 20, 2022

(86) PCT No.: PCT/CN2022/126364

§ 371 (c)(1),
(2) Date: Apr. 17, 2024

(87) PCT Pub. No.: WO2023/066330

PCT Pub. Date: Apr. 27, 2023

(65) Prior Publication Data

US 2025/0017903 A1 Jan. 16, 2025

(30) Foreign Application Priority Data

Oct. 22, 2021 (CN) ......................... 202111232032.0

(51) Int. Cl.
*A61K 31/4152* (2006.01)
*A61P 25/00* (2006.01)

(52) U.S. Cl.
CPC .......... *A61K 31/4152* (2013.01); *A61P 25/00* (2018.01)

(58) Field of Classification Search
CPC ................................................. A61K 31/4152
USPC .......................................................... 514/404
See application file for complete search history.

(56) References Cited

FOREIGN PATENT DOCUMENTS

| | | | |
|---|---|---|---|
| CN | 105616405 | A | 6/2016 |
| CN | 105816423 | A | 8/2016 |
| CN | 105878171 | A | 8/2016 |
| CN | 107773545 | A | 3/2018 |
| CN | 108314652 | A | 7/2018 |
| CN | 108403691 | A | 8/2018 |
| CN | 109431966 | A | 3/2019 |
| CN | 112912072 | A | 6/2021 |
| CN | 113440484 | A | 9/2021 |
| TW | 201912152 | A | 4/2019 |
| WO | 2019213335 | A1 | 11/2019 |

OTHER PUBLICATIONS

Bjorklund, et al., "Oxidative Stress in Autism Spectrum Disorder", Molecular Neurobiology 57, 2314-2332 (2020).
Essa, et al., "Personalized Food Intervention and Therapy for Autism Spectrum Disorder Management", Advances in Neurobiology 24, 20 pages (2020).
Pangrazzi, et al., "Natural Antioxidants: A novel Therapeutic Approach to Autism Spectrum Disorders?", Antioxidants 9 (1186), 18 pages (2020).
Watanabe, et al., "Research and Development of the Free Radical Scavenger Edaravone as a Neuroprotectant", Yakugaku Zasshi 124(3), 99-111, The Pharmaceutical Society of Japan (2004). [English Abstract].
De Mattos, et al., "Quercetin prevents alterations of behavioral parameters, delta-aminolevulinic dehydratase activity, and oxidative damage in brain of rats in a prenatal model of autism", Int J Dev Neurosci 80, 287-302 (2020).
Rossignol, et al., "Evidence linking oxidative stress, mitochondrial dysfunction, and inflammation in the brain of individuals with autism", Frontiers in Physiology 5, article 150, 1-15 (2014).
Chen, J , et al., "Protective effects of edaravone against cobalt chloride-induced apoptosis in PC12 cells", Neurosci Bull 25 (2), 67-74 (2009).
Hata, K , et al., "Pulse radiolysis study on free radical scavenger edaravone (3-methyl-1-phenyl-2-pyrazolin-5-one). 2: A comparative study on edaravone derivatives", J Radiat Res 52 (1), 15-23 (2011).
Maclean, M , et al., "Diversification of edaravone via palladium-catalyzed hydrazine cross-coupling: Applications against protein misfolding and oligomerization of beta-amyloid", Bioorganic & Medicinal Chemistry Letters 26, 100-104 (2016).
Nakagawa, H, et al., "Hydroxyl radical scavenging by edaravone derivatives: Efficient scavenging by 3-methyl-1-(pyridin-2-yl)-5-pyrazolone with an intramolecular base", Bioorganic & Medicinal Chemistry Letters 16, 5939-5942 (2006).
Patent Cooperation Treaty , International Search Report and Written Opinion for PCT/CN2022/126364, 7 pages, dated Dec. 15, 2022.
Wang, L , et al., "A theoretical investigation on DPPH radical-Scavenging mechanism of edaravone", Bioorganic & Medicinal Chemistry Letters 13 (21), 3789-3792 (2003).

*Primary Examiner* — Niloofar Rahmani
(74) *Attorney, Agent, or Firm* — Viksnins Harris Padys Malen LLP

(57) ABSTRACT

The present invention relates to a use of edaravone in the treatment of autism spectrum disorder.

12 Claims, 7 Drawing Sheets

USE OF EDARAVONE IN TREATMENT OF AUTISM SPECTRUM DISORDER

TECHNICAL FIELD

The present invention belongs to the field of pharmaceuticals, and specifically relates to a novel use of edaravone, in particular to a use of edaravone in the preparation of a medicament for treating autism spectrum disorder.

BACKGROUND ART

Autism Spectrum Disorder (ASD) is a neurodevelopmental disorder with a biological basis caused by one or more factors. There is currently no universal specific drug for ASD in the medical field. It exists in all walks of life around the world. The incidence rate in boys is 3 to 4 times higher than in girls. ASD mainly has two core symptoms: social communication disorders, narrow interests and repetitive and stereotyped behaviors. Generally, parents can gradually discover that the child with ASD is different from other children from about 1.5 years old, and the age of diagnosis is generally 3 to 5 years old. In recent years, the incidence of autism have increased year by year based on statistical results. The US Centers for Disease Control released the detection rates of autism in 2007 and 2009 as 1/150 and 1/110 respectively. According to data on 8-year-old children in the United States, the prevalence of autism increased from 1/68 to 1/54 from 2012 to 2020. The estimated number of autistic children in China is nearly 3 million, while the actual number is estimated to be 7 million. The generally high incidence rate of autism has led to current research on autism by scholars, educators, medical workers and other professionals in the field worldwide. Autism has become another killer that affects human life and health in addition to cancer and heart disease.

So far, the pathogenesis of autism is still unclear. Recent studies have suggested that it may be related to a variety of factors, including: 1. Genetic factors (such as copy number variation, single gene mutations (such as Shank3, FMR1), cumulative effects of multi-locus genes, etc.); 2. Epigenetic regulation (including DNA methylation, protein modification-mediated chromatin reorganization, and non-coding RNA, etc.); 3. Abnormal immune response in the brain; 4. Drug exposure during pregnancy (such as Valproic acid (VPA)), etc. The unknown cause of autism makes clinical diagnosis and treatment difficult, and a universal cure has not yet been discovered. At present, the main intervention methods for social-emotional disorders in autism are non-drug intervention programs, that is, social disorder training (such as game therapy, video demonstration method, music therapy, picture exchange communication system (PECS), etc.) and emotional disorder training (emotional recognition and comprehension training, psychological theory training, etc.). However, according to statistics, nearly two-thirds of children with the ASD are unable to live independently after adulthood and require lifelong care and attention, which in turn brings heavy financial and mental pressure to the family and a heavy burden to society. Therefore, there is an urgent clinical need for drug treatment options.

Edaravone (EDA) is one of pyrazolone derivatives. Its chemical name is 3-methyl-1-phenyl-2-pyrazolin-5-one, and its molecular formula is $C_{10}H_{10}N_2O$. Its structural formula is as follows:

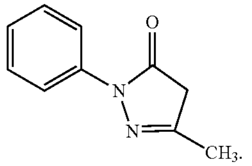 [SMILES: CC1=NN(c2ccccc2)C(=O)C1]

The core structure or active center of EDA is 2-pyrazolin-5-one, which plays a major role in free radical scavenging activity. The substituents have little effect on the activity (Bioorg. Med. Chem. Lett. 13 (2003) 3789-3792).

EDA is a nitrogen-containing heterocyclic compound, which is alkaline and easily reacts with acid to form a salt. The pharmaceutically acceptable salts thereof include common inorganic acid salts and organic acid salts in the field, wherein the inorganic acid salts include hydrochlorides, carbonates, phosphates, etc., and the organic acid salts include citrates, tartrates, acetates, oxalates, salicylates, malates, lactates, etc.

EDA analogues include those wherein the methyl group located at position 3 of the pyrazoline ring is replaced with lower ($C_{1-6}$) alkyl group such as ethyl and propyl, or lower alkoxy group such as methoxy, ethoxy, etc.; or those wherein the methyl group at position 3 is replaced with H, and the H at position 4 is replaced with lower alkyl or alkoxy. Derivatives of edaravone include esters, that is, the ketone at position 5 of the pyrazoline ring is converted into enol (J. Radiat. Res., 52, 15-23 (2011)), and reacts with carboxylic acid to form esters, such as methyl ester, ethyl ester, etc. The ester (precursor) is hydrolyzed in the body and then converted into ketones. In addition, the phenyl group is also optionally substituted by one or more substituents selected from lower alkyl, lower alkoxy, nitro, halogen, etc.

EDA derivatives include as many as 18 EDA derivatives with similar oxidation potential (Epa) and hydroxyl radical scavenging activity ($IC_{50}$) disclosed in Tables 1-2 and FIG. 2 of Bioorg. Med. Chem. Lett. 16 (2006), in which the benzene ring ($R^1$), position 3 ($R^3$) and position 4 ($R^4$) can be further modified.

EDA derivatives include 21 EDA derivatives confirmed in Bioorg. Med. Chem. Lett. (2015), which have the same anti-aggregation properties (http://dx.doi.org/10.1016/j.bmcl.2015.11.022).

EDA derivatives also include compounds of formula (I) disclosed in CN patent application No. 201710036907.7, especially compounds of formula (Ia) (BE). The entire content of this patent application document is incorporated herein by reference.

Edaravone is a strong synthetic scavenger of oxygen free radical with antioxidant effects to reduce oxidative stress and inhibit lipid peroxidation via non-enzymatic lipid peroxidation and lipoxygenase pathways. Edaravone was first developed by Mitsubishi Tanabe Pharm Corp. (Osaka, Japan) and was used to improve neurological symptoms, daily living activities and dysfunction caused by acute cerebral infarction. The marketed dosage form is injection. At present, edaravone has been widely used worldwide to treat acute ischemic stroke (AIS), and is also used to treat excess reactive oxygen species (ROS)-related diseases, such as cardiovascular disease and stroke.

CN105816423B discloses various preparations of edaravone (such as solid phase dispersion preparations) and their use in effectively treating oxidative stress-related diseases in humans; CN108403691A discloses that edaravone can be used to prevent and treat cataracts; CN105616405A discloses that edaravone directly acts on Aβ, inhibits Aβ aggregation and promotes Aβ fiber depolymerization, thereby blocking or delaying the progression of cerebral amyloid angiopathy (CAA); CN109431966A discloses an edaravone pharmaceutical composition and its sublingual preparation comprising edaravone or a salt thereof and mannitol; CN107773545A discloses a sublingual pharmaceutical composition comprising edaravone and (+)-2-camphol; and CN105878171A discloses a nasal administration preparation of edaravone (the contents of the above 6 patent application documents are all incorporated herein by reference).

CN112912072A discloses a method for treating or slowing down the progression of neuronal inflammation in a subject in need thereof, comprising co-administering a first compound and a second compound, wherein the first compound and the second compound are independently (a) a compound of formula (I), . . . (c) Edaravone or riluzole, . . . (e) nonsteroidal anti-inflammatory drugs (NSAIDs), or (f) anti-inflammatory peptides. It further specifically discloses that the first compound is cromolyn sodium, the second compound is an NSAID, and wherein the neuronal inflammation is ALS, ASD, ischemic stroke and prion disease.

TW201912152A discloses a method for treating or preventing neurological disorders and the like, which includes administering d-methadone and the like to an individual. It also teaches that d-methadone can be used in combination with edaravone, and neurological disorders include AD, ASD, etc.

However, there are no reports of edaravone being administrated alone to treat autism spectrum disorder (ASD) in the prior art.

SUMMARY OF THE INVENTION

An object of the present invention is to provide a novel use of edaravone, that is, for treating autism spectrum disorder (ASD).

First, the present invention provides a use of edaravone or a pharmaceutically acceptable salt or an analog or a derivative thereof (preferably as a sole active ingredient alone) in the preparation of a medicament for treating autism spectrum disorder (ASD).

On the other hand, the present invention also provides a pharmaceutical composition for treating autism spectrum disorder, comprising edaravone or a pharmaceutically acceptable salt or an analog or a derivative thereof, and one or more pharmaceutically acceptable excipients.

According to the present invention, edaravone can also be administrated in combination (sequentially or simultaneously) with one or more other drugs for treating ASD (such as cromolyn/salt, NSAID, d-methadone, etc.), or constitute a pharmaceutical composition with one or more other drugs for treating ASD (e.g., including, but not limited to, cromolyn/salt, NSAID, and d-methadone).

According to the present invention, the administration mode of the pharmaceutical composition is intravenous drip, intramuscular injection, oral, transdermal, sublingual, intranasal, intraocular, inner ear, rectal, or intravaginal routes. Preferably, the administration mode of the pharmaceutical composition is oral administration.

In one embodiment of the present invention, the pharmaceutical dosage form for oral administration is a solid preparation, preferably a solid phase dispersion preparation, which comprises edaravone or a pharmaceutically acceptable salt thereof as an active ingredient, a polymer carrier which is selected from Soluplus, polyethylene glycol (PEG), hydroxypropyl methylcellulose (HPMC), hydroxypropyl methylcellulose acetate (HPMCAS), hydroxypropyl cellulose (HPC) and chitosan (preferably Soluplus and/or HPMC, more preferably Soluplus), and optionally, a surfactant TPGS 1000. In the pharmaceutical composition, the unit dose of edaravone is 0.001-1000 mg, preferably 0.01-500 mg, more preferably 0.1-100 mg, most preferably 1-50 mg, such as 1 mg, 2 mg, 3 mg, 4 mg, 5 mg, 10 mg, 15 mg, 20 mg, 25 mg, 30 mg, 35 mg, 40 mg, 45 mg and 50 mg.

The present invention relates to a method for treating autism spectrum disorder (ASD) with edaravone or a pharmaceutically acceptable salt or an analog or a derivative thereof, which comprises administering to a subject in need thereof a therapeutically effective amount of edaravone or a pharmaceutically acceptable salt or an analog or a derivative thereof.

The present invention also relates to edaravone or a pharmaceutically acceptable salt or an analog or a derivative thereof for treating autism spectrum disorder (ASD), or a medicament for treating autism spectrum disorder (ASD) comprising edaravone or a pharmaceutically acceptable salt or an analog or a derivative thereof.

The present invention unexpectedly found that edaravone has great efficacy in treating autism spectrum disorder, especially in improving social disorders and stereotyped behaviors.

Definitions

The term "pharmaceutically acceptable" means approved for use in animals, preferably in humans, by a regulatory agency such as EMEA (Europe) and/or FDA (US) and/or any other national regulatory agency.

The term "excipient" refers to a diluent, adjuvant or carrier with which a therapeutic agent is administered. Examples of suitable pharmaceutical excipients are described in "Remington's Pharmaceutical Sciences" by E. W. Martin.

The present invention provides a suitable administration mode of edaravone for treating autism spectrum disorder. Taking into account the convenience of administration and to increase the medication compliance of patients, oral administration is preferred.

The preparation method of the present oral administration preparation can be obtained by referring to conventional methods in the art. It is particularly preferred to refer to the method disclosed in CN105816423B for preparing the oral administration preparation of edaravone or a pharmaceutically acceptable salt thereof.

In the present invention, edaravone or a pharmaceutically acceptable salt or an analog or a derivative thereof is sometimes collectively referred to as "edaravone" and are used interchangeably.

According to the present invention, the administration dosage of edaravone is between 0.1 mg/kg and 100 mg/kg. For treatment, the administration dosage is preferably 0.1-50 mg/kg, such as 0.1 mg/kg, 0.5 mg/kg, 1.0 mg/kg, 2.0 mg/kg, 3.0 mg/kg, 5.0 mg/kg, 10.0 mg/kg, 15 mg/kg, 20 mg/kg, 25 mg/kg, 30 mg/kg, 35 mg/kg, 40 mg/kg, 45 mg/kg or 50 mg/kg, etc., twice a day to twice a week.

The dosage and frequency of administration of the present preparation can be varied according to the patient conditions, and sometimes require relatively short intervals and relatively high doses (for example, 5.0-35 mg/kg) until the progression of the disease is alleviated or terminated, preferably until the patient exhibits partial or complete improvement of disease symptoms. The present medicaments may be administered parenterally, topically, intravenously, orally, subcutaneously, intraarterially, intracranially, intrathecally, intraperitoneally, intranasally or intramuscularly. The typical route of administration is oral, followed by intramuscular injection, although other routes are equally effective. Intramuscular injection is most commonly given into the arm or leg muscles.

BRIEF DESCRIPTION OF THE DRAWINGS

In order to illustrate the technical solutions of the present invention more clearly, a brief introduction will be given below with reference to the accompanying drawings. Obviously, these drawings are only some particular embodiments described in this application. The present invention includes, but is not limited to, these drawings.

DETAILED DESCRIPTION OF THE INVENTION

In order to further understand the present invention, the preferred embodiments of the present invention will be described below in conjunction with examples. These descriptions only illustrate the features and advantages of the technical solutions of the present invention, but do not limit the scope of protection of the present invention.

The Aim of the Experiment

To test the therapeutic effect of edaravone in valproic acid (VPA)-induced rat autism model.

Establishment of an Autism Model

Twenty-five SD pregnant rats were given a single intraperitoneal injection of 500 mg/kg sodium valproate (VPA) on 12.5 embryonic day and delivered on 21 embryonic day, and the male offspring were retained as the VPA group. Five pregnant rats in the control group were given a single intraperitoneal injection of normal saline of the same amount on 12.5 embryonic day and delivered on 21 embryonic day; and the male offspring were designated as the CON group.

Figure 1:
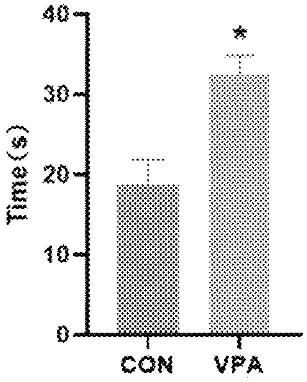
FIG. 1 shows the comparison of grooming time between the VPA modeled group and the normal group after modeling.
Figure 2:
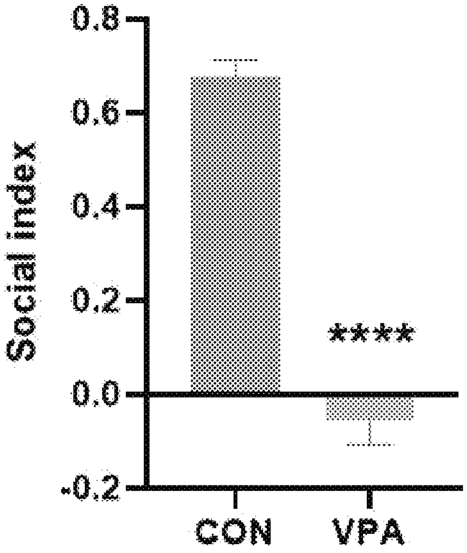
FIG. 2 shows the results of the three-chamber social test of the VPA modeled group and the normal group after modeling.

When the offspring rats were $25^{th}$ day old, an open field test was conducted to observe the grooming time, which reflects the repetitive and stereotyped behaviors of the animals); a three-chamber social test was conducted to observe the Social Index (SI), Social Index=(Time when the animal enters the unfamiliar rat area-time when the animal enters the empty cage area)÷(time when the animal enters the unfamiliar rat area+time when the animal enters the empty cage area), reflecting the social ability of experimental animals. The results showed that compared with the CON group, the grooming time of animals in the VPA group was significantly increased (FIG. 1, $p<0.005$). In the three-chamber social test, compared with the CON group, the social index (SI) of animals in the VPA group was significantly reduced (FIG. 2, $p<0.0001$). The above results demonstrate that animals in the VPA group showed obvious social disorders and repetitive and stereotyped behaviors, and the modeling was successful.

Animal Grouping, Administration, and Testing

On the $26^{th}$ day after the offspring were born, the modeled VPA group was randomly divided into 6 groups: placebo group (n=19, soluplus 428 mg/kg), positive drug (cromolyn sodium) group (n=14, cromolyn sodium 6.3 mg/kg), positive drug solvent (NS) group (n=12, equal dose of normal saline), EDA low-dose group (n=12, Edaravone 3 mg/kg), EDA medium-dose group (n=12, Edaravone 10 mg/kg) and EDA high-dose group (n=22, Edaravone 30 mg/kg); and another CON group (n=9). The positive drug group and the positive drug solvent group were given intraperitoneal injection, and the placebo group and each dose group of EDA were administrated by oral gavage, once a day for 28 consecutive days. Three-chamber social tests were conducted after 14 and 28 days of administration, and an open field test was conducted after 28 days of administration. After the animals were sacrificed, 6 animals were randomly selected from each group of the placebo group and each dose group of EDA, and the prefrontal cortex, hippocampus, cerebellum and blood were collected to detect oxidative stress-related indicators, so as to detect the antioxidant capacity of the body.

Results

1. Results of the Three-Chamber Social Test

Figure 3:
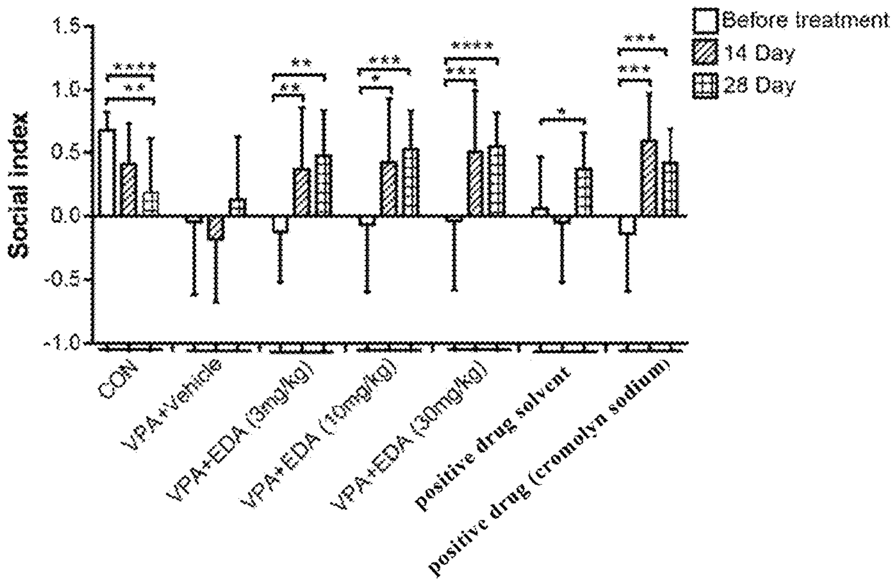
FIG. 3 shows the before and after self-comparison of the social index (SI) of experimental animals after 14 and 28 days of treatment.
Figure 4:
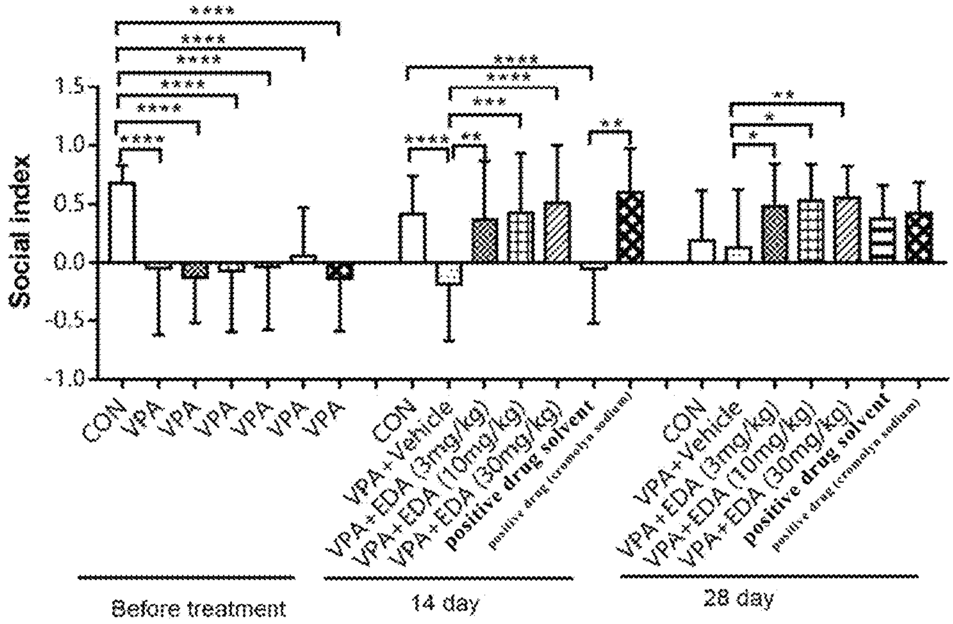
FIG. 4 shows the inter-group comparison of the social index (SI) of experimental animals after 14 and 28 days of treatment.

The social index (SI) of animals in each group before gavage treatment, 14 days and 28 days after gavage treatment is shown in Table 1. Compared with before treatment, the social index of animals in each dose group of EDA was increased significantly after 14 and 28 days of continuous gavage treatment, and the 28-day treatment effect was better than that of 14 days (FIG. 3); inter-group comparison showed that before treatment, compared with the CON group, the social index of animals in each model group was significantly reduced; after 14 days of treatment, compared with the placebo group, the social index of animals in each dose group of EDA and the positive drug (cromolyn sodium) group was significantly improved ($p<0.01$), among which the EDA medium-dose group and the high-dose group had better effects ($p<0.001$, $p<0.0001$); after 28 days of treatment, compared with the placebo group, the social index of animals in each dose group of EDA was significantly improved ($p<0.05$), and the high-dose EDA group had better effects (p<0.01), while there was no significant difference between the positive drug (cromolyn sodium) and positive drug solvent groups (FIG. 4). It shows that edaravone can significantly improve the social index and ameliorate the social impairment of VPA-induced autism model rats.

TABLE 1

Social index (SI) of animals before gavage treatment, 14 days and 28 days after gavage treatment (mean ± SE)

| Group | Before treatment | Day 14 | Day 28 |
|---|---|---|---|
| CON | 0.68 ± 0.04 | 0.41 ± 0.08 | 0.19 ± 0.09 |
| VPA + Vehicle | −0.04 ± 0.13 | −0.18 ± 0.11 | 0.13 ± 0.11 |
| VPA + EDA (3 mg/kg) | −0.12 ± 0.11 | 0.37 ± 0.14 | 0.48 ± 0.10 |
| VPA + EDA (10 mg/kg) | −0.07 ± 0.15 | 0.42 ± 0.15 | 0.53 ± 0.09 |
| VPA + EDA (30 mg/kg) | −0.04 ± 0.12 | 0.51 ± 0.11 | 0.55 ± 0.06 |
| Positive drug solvent | 0.06 ± 0.12 | −0.04 ± 0.14 | 0.37 ± 0.08 |
| Positive drug (cromolyn sodium) | −0.13 ± 0.12 | 0.08 ± 0.37 | 0.42 ± 0.07 |

2. Results of the Open Field Test after 28 Days of Treatment

Figure 5:
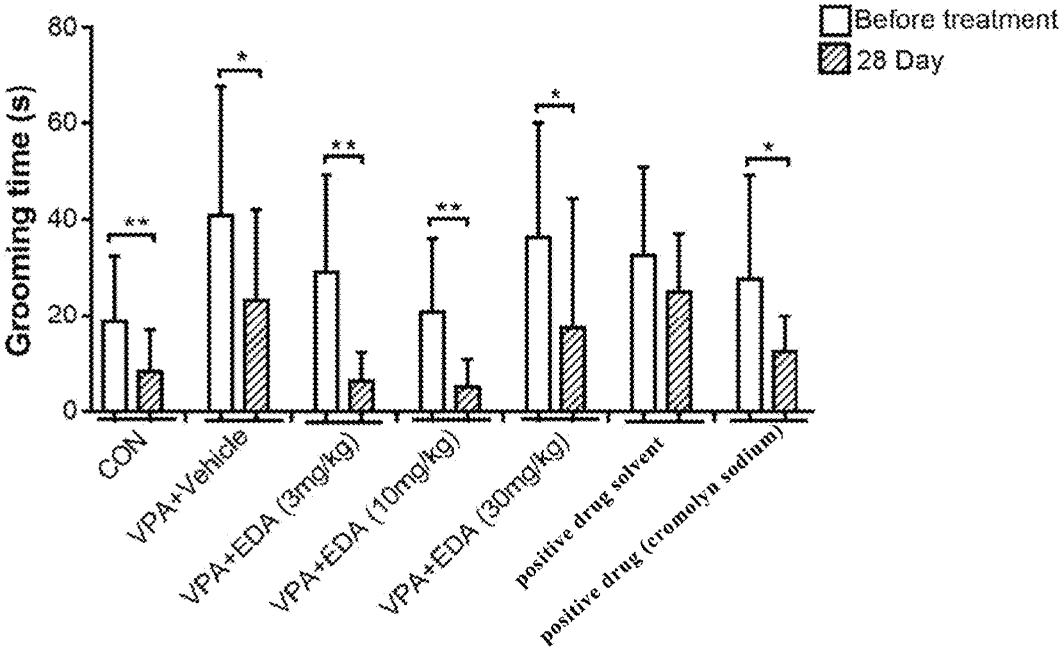
FIG. 5 shows the before and after self-comparison of the grooming time of experimental animals after 28 days of treatment.
Figure 6:
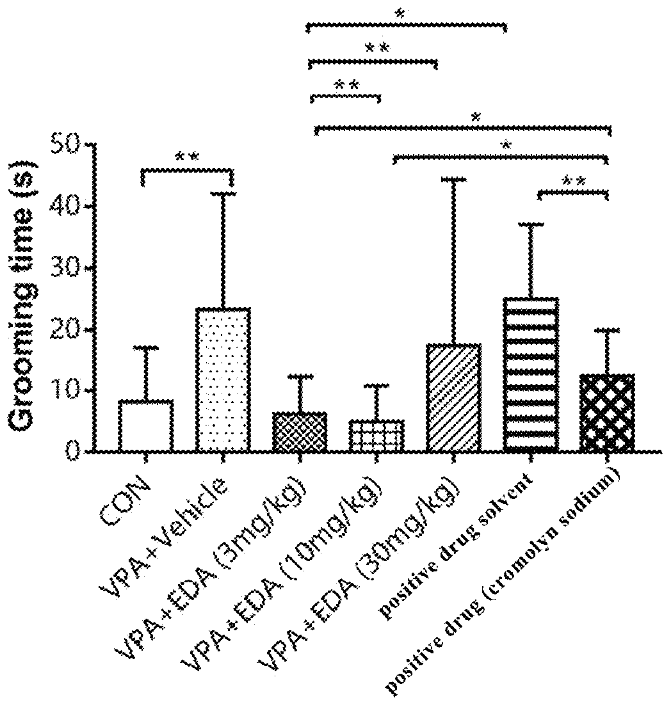
FIG. 6 shows the inter-group comparison of the grooming time of experimental animals after 28 days of treatment.

The grooming time of animals in each group before gavage treatment and 28 days after gavage treatment is shown in Table 2. Compared with before treatment, after 28 days of continuous gavage treatment, the grooming time of animals in each dose group of EDA, as well as the placebo group and the positive drug (cromolyn) group was significantly reduced (p<0.05). Among them, the differences between the EDA low-dose group and the EDA medium-dose group were more significant (p<0.01) (FIG. 5). Inter-group comparison showed that after 28 days of continuous gavage treatment, compared with the placebo group, the grooming time of animals in each dose group of EDA was significantly reduced (p<0.05), among which the differences between the EDA low-dose group and the EDA medium-dose group were more significant (p<0.01), and there was no significant difference between the positive drug solvent group and the positive drug (cromolyn sodium) group; compared with the positive drug (cromolyn sodium) group, the grooming time of animals in the EDA low-dose group and the EDA medium-dose group was significantly reduced (FIG. 6). This shows that edaravone can significantly reduce the grooming time and ameliorate the repetitive and stereotyped behaviors of VPA-induced autism model rats.

TABLE 2

Grooming time of animals before gavage treatment and after 28 days of gavage treatment (mean ± SE)

| Group | Before treatment | Day 28 |
|---|---|---|
| CON | 11.87 ± 1.68 | 10.86 ± 3.34 |
| VPA + Vehicle | 40.87 ± 6.19 | 23.32 ± 4.31 |
| VPA + EDA (3 mg/kg) | 29.17 ± 5.82 | 6.29 ± 1.72 |
| VPA + EDA (10 mg/kg) | 20.76 ± 4.42 | 5.04 ± 1.67 |
| VPA + EDA (30 mg/kg) | 36.3 ± 5.08 | 17.27 ± 5.78 |
| Positive drug solvent | 32.63 ± 5.27 | 25.05 ± 3.48 |
| Positive drug (cromolyn sodium) | 27.63 ± 5.78 | 12.41 ± 2.01 |

3. Oxidative Stress Indicators

Figure 7:
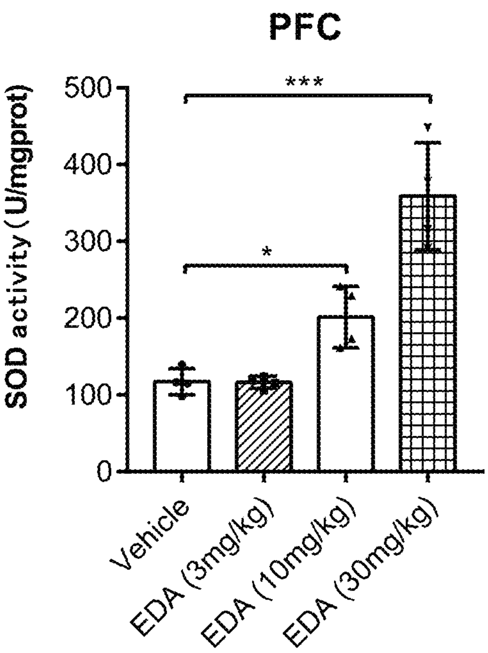
FIG. 7 shows the results of SOD activity detection in the prefrontal cortex (PFC)
Figure 8:
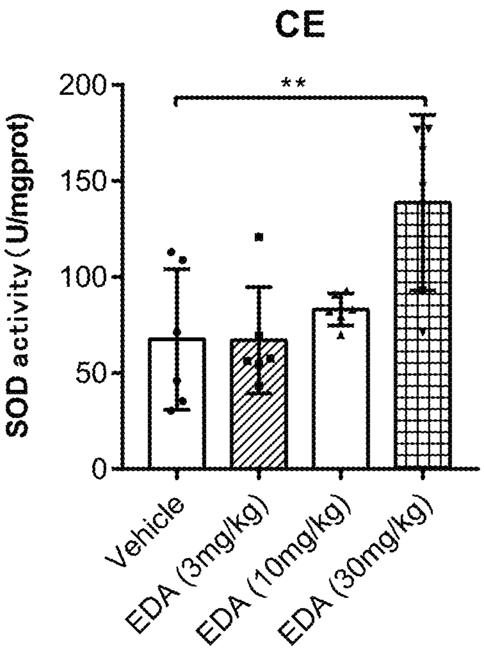
FIG. 8 shows the results of SOD activity detection in the cerebellum (CE)

After 28 days of gavage treatment, the results of superoxide dismutase (SOD) activity detection in the prefrontal cortex (PFC) and cerebellum (CE) are shown in Table 3. The results showed that compared with the placebo group, the SOD activity in the prefrontal cortex of the EDA medium-dose group and high-dose group was significantly increased (p<0.05), and the increase was more obvious in the EDA high-dose group (p<0.001) (FIG. 7); The SOD activity in the cerebellum of the EDA high-dose group was significant (p<0.01) (FIG. 8).

TABLE 3

SOD activity in PFC and CE regions of rats after 28 days of gavage treatment (mean ± SE)

| Group | SOD activity (U/mgprot) in the prefrontal cortex (PFC) | SOD activity (U/mgprot) in the cerebellum (CE) |
|---|---|---|
| VPA + Vehicle | 130.8 ± 10.3 | 67.52 ± 14.92 |
| VPA + EDA (3 mg/kg) | 124.6 ± 5.73 | 67.04 ± 11.3 |
| VPA + EDA (10 mg/kg) | 203.4 ± 14.37 | 83.07 ± 3.39 |
| VPA + EDA (30 mg/kg) | 315 ± 42.53 | 138.7 ± 18.62 |

Figure 9:
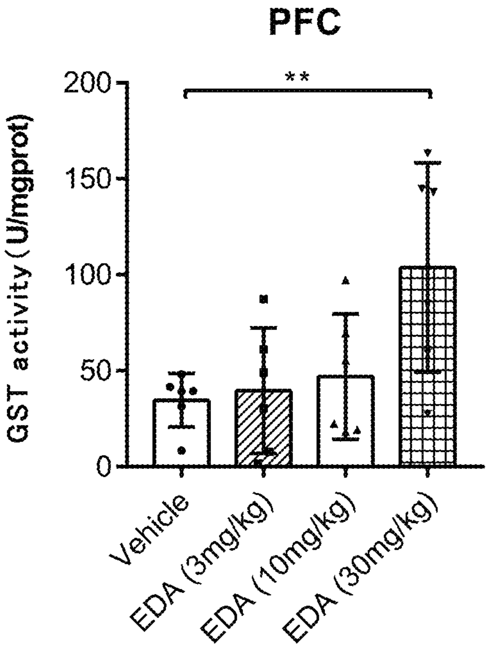
FIG. 9 shows the results of GST activity detection in the prefrontal cortex (PFC)
Figure 10:
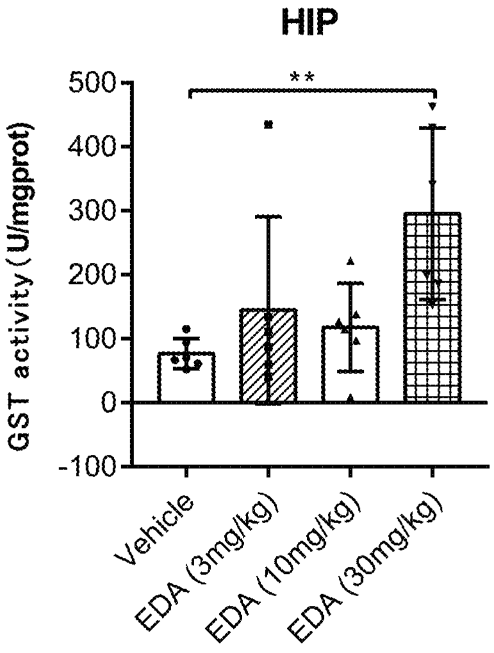
FIG. 10 shows the results of GST activity detection in the hippocampus (HIP)

After 28 days of gavage treatment, the results of glutathione S-transferase (GST) activity detection in the prefrontal cortex (PFC) and hippocampus (HIP) are shown in Table 4. The results showed that compared with the placebo group, the GST activity in the prefrontal cortex (PFC) and hippocampus (HIP) in the high-dose EDA group was significantly increased (p<0.01) (FIGS. 9, 10).

TABLE 4

GST activity in PFC and HIP regions of rats after 28 days of gavage treatment (mean ± SE)

| Group | GST activity (U/mgprot) in the prefrontal cortex (PFC) | GST activity (U/mgprot) in the hippocampus (HIP) |
|---|---|---|
| VPA + Vehicle | 34.63 ± 5.68 | 76.76 ± 9.62 |
| VPA + EDA (3 mg/kg) | 39.54 ± 13.34 | 144.5 ± 59.64 |
| VPA + EDA (10 mg/kg) | 46.93 ± 13.31 | 117.7 ± 28.12 |
| VPA + EDA (30 mg/kg) | 103.8 ± 22.27 | 295.4 ± 54.67 |

Figure 11:
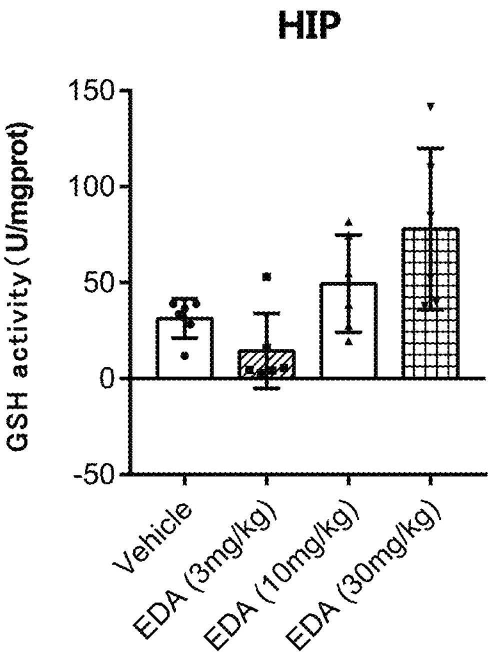
FIG. 11 shows the results of GSH activity detection in the hippocampus (HIP)
Figure 12:
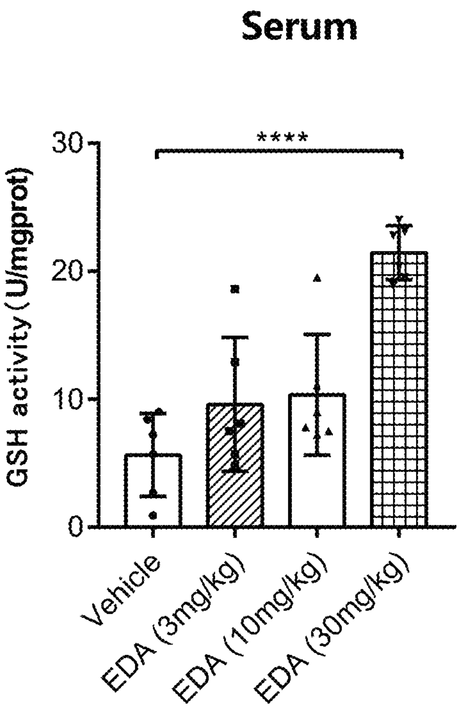
FIG. 12 shows the results of GSH activity detection in serum.

After 28 days of gavage treatment, the results of reduced glutathione (GSH) activity detection in hippocampus (HIP) and serum are shown in Table 5. The results showed that compared with the placebo group, the GSH activity in the hippocampus (HIP) of the EDA high-dose group was significantly increased (p<0.05) (FIG. 11), and the GST activity in the serum was even more significantly increased (p<0.01) (FIG. 12).

TABLE 5

GSH activity in HIP and serum of rats after 28 days of gavage treatment (mean ± SE)

| Group | GSH activity (U/mgprot) in the hippocampus (HIP) | GSH activity (U/mgprot) in the serum |
|---|---|---|
| VPA + Vehicle | 31.33 ± 4.2 | 5.65 ± 1.32 |
| VPA + EDA (3 mg/kg) | 14.44 ± 7.97 | 9.6 ± 2.14 |
| VPA + EDA (10 mg/kg) | 49.39 ± 10.34 | 10.35 ± 1.92 |
| VPA + EDA (30 mg/kg) | 78.87 ± 17.13 | 21.45 ± 0.86 |

Figure 13:
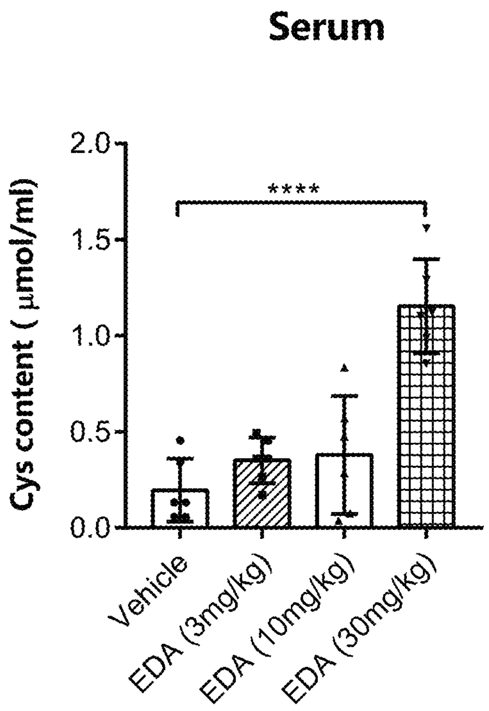
FIG. 13 shows the results of Cys content detection in serum.

After 28 days of gavage treatment, the test results of cysteine (Cys) content in serum are shown in Table 6. The results showed that after 28 days of treatment, the Cys content in the blood of animals in the EDA high-dose group was significantly higher than that in the placebo group (p<0.0001) (FIG. 13).

TABLE 6

| Cys content in serum after 28 days of gavage treatment (mean ± SE) | |
|---|---|
| Group | Cys content in serum (μmol/mL) |
| VPA + Vehicle | 0.20 ± 0.07 |
| VPA + EDA (3 mg/kg) | 0.35 ± 0.05 |
| VPA + EDA (10 mg/kg) | 0.38 ± 0.13 |
| VPA + EDA (30 mg/kg) | 1.15 ± 0.10 |

The test results of oxidative stress indicators showed that edaravone can improve the antioxidant capacity of VPA-induced autism model rats.

The above description of specific embodiments is only used to help understand the core idea of the present invention. It should be noted that for those skilled in the art, several improvements and modifications can be made to the technical solutions of the present invention without departing from the principles of the present invention, and these improvements and modifications also fall within the scope of the claims of the present invention.

The invention claimed is:

1. A method of treating autism spectrum disorder (ASD), which comprises administering to a subject in need thereof an effective amount of a medicament, which medicament comprises edaravone or a pharmaceutically acceptable salt, analog, or derivative thereof.

2. The method of claim 1, wherein the medicament further comprises one or more pharmaceutically acceptable excipients.

3. The method of claim 2, wherein the medicament is administered by intravenous drip, intramuscular injection, or by an oral, transdermal, sublingual, intranasal, intraocular, inner ear, rectal, or intravaginal route.

4. The method of claim 1, wherein the medicament is a solid preparation.

5. The method of claim 4, wherein the one or more pharmaceutically acceptable excipients comprise a polymer carrier and an optional surfactant; wherein the polymer carrier is Soluplus®, polyethylene glycol (PEG), hydroxypropyl methylcellulose (HPMC), hydroxypropyl methylcellulose acetate (HPMCAS), hydroxypropyl cellulose (HPC), or chitosan; and the optional surfactant is TPGS 1000.

6. The method of claim 5, wherein the medicament is administered as a single unit dosage form containing an amount of edaravone or a pharmaceutically acceptable salt, analog, or derivative thereof, which amount is 0.001-1000 mg.

7. The method of claim 1, wherein the effective amount is 0.1-100 mg/kg.

8. The method of claim 3, wherein the medicament is administered orally.

9. The method of claim 4, wherein the solid preparation is a solid dispersion.

10. The method of claim 6, wherein the amount is 0.1-100 mg.

11. The method of claim 10, wherein the amount is 1-50 mg.

12. The method of claim 7, wherein the effective amount is 1-30 mg/kg.

* * * * *